(12) United States Patent
Kang et al.

(10) Patent No.: US 10,987,089 B2
(45) Date of Patent: Apr. 27, 2021

(54) ULTRASOUND IMAGING APPARATUS AND METHOD OF GENERATING ULTRASOUND IMAGE

(71) Applicant: SAMSUNG MEDISON CO., LTD., Hongcheon-gun (KR)

(72) Inventors: Ho-kyung Kang, Seoul (KR); Jong-geun Park, Seoul (KR); Ki-won Sohn, Seoul (KR); Won-chul Bang, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 166 days.

(21) Appl. No.: 15/343,508

(22) Filed: Nov. 4, 2016

(65) Prior Publication Data

US 2017/0128050 A1 May 11, 2017

Related U.S. Application Data

(60) Provisional application No. 62/251,251, filed on Nov. 5, 2015.

(30) Foreign Application Priority Data

Mar. 15, 2016 (KR) .................. 10-2016-0030987

(51) Int. Cl.
*A61B 8/14* (2006.01)
*A61B 8/08* (2006.01)
(Continued)

(52) U.S. Cl.
CPC ............ *A61B 8/5215* (2013.01); *A61B 8/463* (2013.01); *A61B 8/465* (2013.01); *A61B 8/467* (2013.01);
(Continued)

(58) Field of Classification Search
CPC ...... G01S 15/00; G01S 15/89; G01S 7/52095; G01S 15/8963; G01S 15/8979; G01S 15/8993; G01S 7/52025; G01S 7/5208; G01S 15/8925; G01S 7/52074; G01S 15/8918; G01S 15/894; G10K 11/00; G10K 11/34; G10K 11/341; A61B 8/06;
(Continued)

(56) References Cited

U.S. PATENT DOCUMENTS 6,419,632 B1 7/2002 Shiki et al.
6,638,228 B1 10/2003 Brock-Fisher et al.
2002/0045830 A1* 4/2002 Powers .................. A61B 8/06
600/459

FOREIGN PATENT DOCUMENTS

JP 2000342586 A 12/2000
JP 2004129967 A 4/2004
JP 200982181 A 4/2009

* cited by examiner

*Primary Examiner* — Jon Eric C Morales
(74) *Attorney, Agent, or Firm* — Sughrue Mion, PLLC

(57) ABSTRACT

Provided are an ultrasound imaging apparatus and method of generating an ultrasound image. The ultrasound imaging apparatus includes: a memory configured to store instructions; and at least one processor configured to execute the stored instructions to: generate, based on echo signals reflected from an object, a first image showing a tissue of the object and a second image showing a contrast medium injected into the object; generate a third image by removing at least a portion of the tissue from the second image based on the first image; and display the generated third image.

19 Claims, 11 Drawing Sheets

(51) Int. Cl.
*A61B 8/00* (2006.01)
*G01S 7/52* (2006.01)
(52) U.S. Cl.
CPC ............. *A61B 8/481* (2013.01); *A61B 8/486* (2013.01); *A61B 8/488* (2013.01); *A61B 8/5207* (2013.01); *A61B 8/5246* (2013.01); *G01S 7/52039* (2013.01); *G01S 7/52074* (2013.01)
(58) Field of Classification Search
CPC ..... A61B 8/0883; A61B 8/0891; A61B 8/481; A61B 8/483; A61B 8/4472; A61B 8/543; Y10S 128/916
USPC ......................................................... 600/459
See application file for complete search history.

FIG. 4B
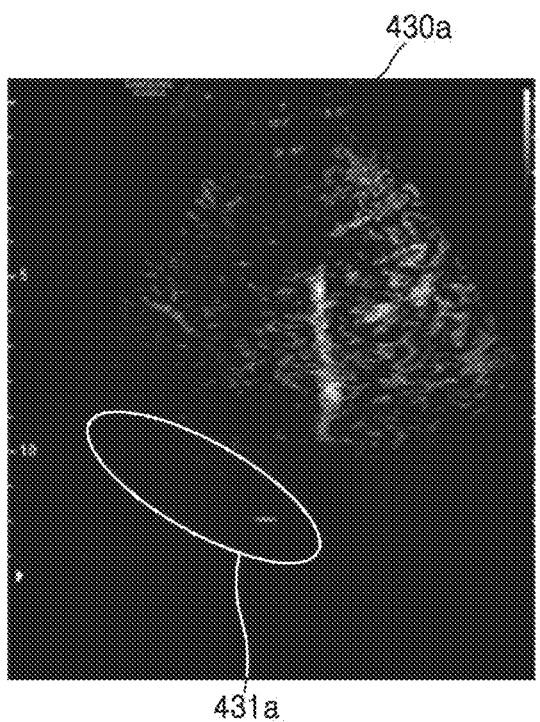

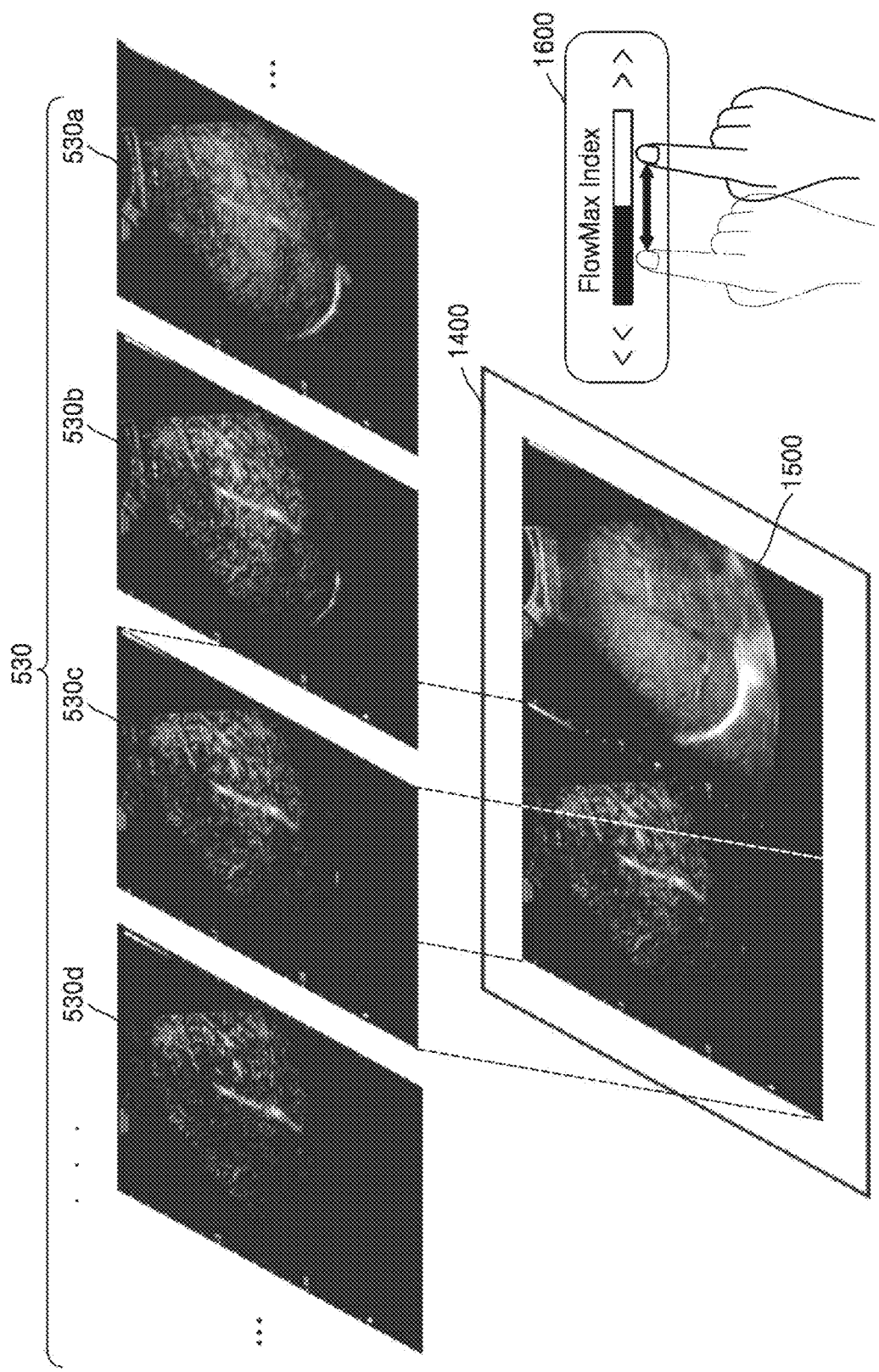

ULTRASOUND IMAGING APPARATUS AND METHOD OF GENERATING ULTRASOUND IMAGE

CROSS-REFERENCE TO RELATED APPLICATIONS

This application claims the benefit of U.S. Provisional Application No. 62/251,251, filed on Nov. 5, 2015, in the US Patent Office and Korean Patent Application No. 10-2016-0030987, filed on Mar. 15, 2016, in the Korean Intellectual Property Office, the disclosures of which are incorporated herein in their entireties by reference.

BACKGROUND

1. Field

The present disclosure relates to ultrasound imaging apparatuses and methods of generating an ultrasound image by using the same, and more particularly, to methods and apparatuses for generating an ultrasound image from which at least a portion of a tissue is removed.

2. Description of the Related Art

Ultrasound imaging apparatuses transmit ultrasound signals generated by transducers of a probe to an object and receive echo signals reflected from the object, thereby obtaining at least one image of an internal part of the object (e.g., soft tissues or blood flow). In particular, ultrasound imaging apparatuses are used for medical purposes including observing an inner area of an object, detecting foreign substances, and assessing injuries. Such ultrasound imaging apparatuses provide high stability, display images in real time, and are safe due to there being no radiation exposure, compared to X-ray apparatuses. Therefore, ultrasound imaging apparatuses are widely used together with other image imaging apparatuses including a computed tomography (CT) apparatus, a magnetic resonance imaging (MRI) apparatus, and the like.

Among imaging methods using an ultrasound system, contrast-enhanced ultrasound (CEUS) imaging involves the administration of a contrast medium to an object. Examination using a CEUS image allows a user to quantitatively determine whether an object such as a tumor is malignant or benign by observing a tendency of image signal values of the object over time after injection of the contrast medium into the object.

SUMMARY

Provided are ultrasound imaging apparatuses and methods of generating an ultrasound image by using the same so that a contrast-enhanced image from which at least a portion of a tissue is removed may be obtained.

Provided are ultrasound imaging apparatuses and methods of generating an ultrasound image so that a contrast-enhanced image with improved contrast between blood vessels and tissue may be obtained.

According to an aspect of an embodiment, an ultrasound imaging apparatus includes: a memory configured to store instructions; and at least one processor configured to execute the stored instructions to: generate, based on echo signals reflected from an object, a first image showing a tissue of the object and a second image showing a contrast medium injected into the object; generate a third image by removing at least a portion of the tissue from the second image based on the first image; and display the generated third image.

According to an aspect of another embodiment, a method of generating an ultrasound image includes: generating, based on echo signals reflected from an object, a first image showing a tissue of the object and a second image showing a contrast medium injected into the object; generating a third image by removing at least a portion of the tissue from the second image based on the first image; and displaying the generated third image.

According to an aspect of another embodiment, a computer-readable recording medium has recorded thereon a program for executing the method of generating an ultrasound image on a computer.

BRIEF DESCRIPTION OF THE DRAWINGS

FIG. 4B is an exemplary diagram of third and fourth images according to an embodiment;

FIG. 5 is an exemplary diagram of a user interface (UI) for displaying a plurality of contrast-enhanced ultrasound images, according to an embodiment;

DETAILED DESCRIPTION

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used herein have to be defined based on the meaning of the terms together with the description throughout the specification.

When a part "includes" or "comprises" an element, unless there is a particular description contrary thereto, the part can further include other elements, not excluding the other elements. In addition, terms such as " . . . unit", " . . . module", or the like refer to units that perform at least one function or operation, and the units may be implemented as hardware or software or as a combination of hardware and software.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

Furthermore, in the present specification, the terms "first", "second", "1-1", etc. are only used to distinguish one component, element, object, image, pixel, or patch from another component, element, object, image, pixel, or patch. Thus, these terms are not limited to representing the order or priority among elements or components. Expressions such as "at least one of," when preceding a list of elements, modify the entire list of elements and do not modify the individual elements of the list.

Embodiments will now be described more fully hereinafter with reference to the accompanying drawings.

Figure 1:
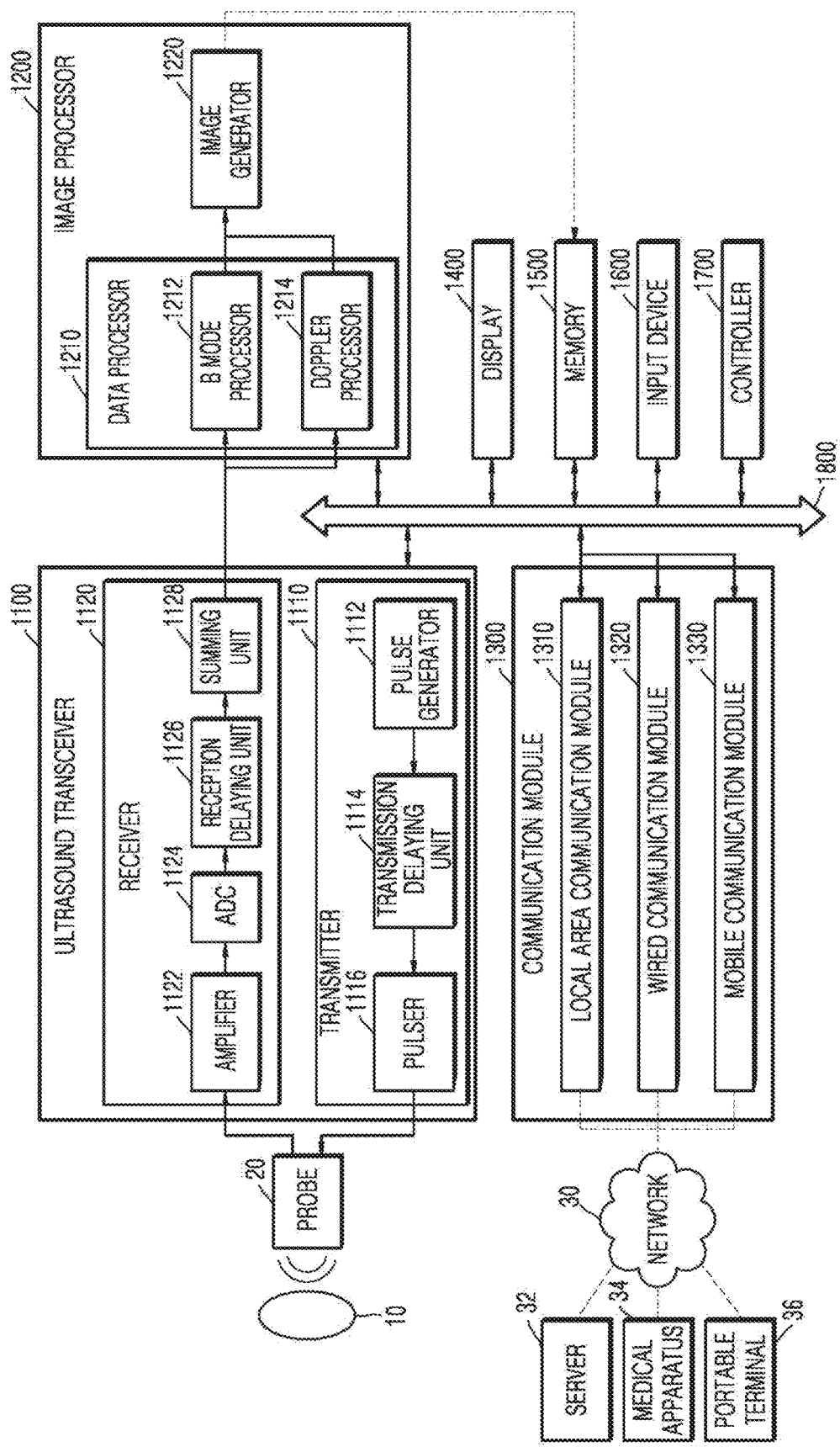
FIG. 1 is a block diagram of a configuration of an ultrasound imaging apparatus according to an embodiment.

FIG. 1 is a block diagram of a configuration of an ultrasound imaging apparatus 1000 according to an embodiment Referring to FIG. 1, the ultrasound imaging apparatus 1000 may include a probe 20, an ultrasound transceiver 1100, an image processor 1200, a communication module 1300, a display 1400, a memory 1500, an input device 1600, and a controller 1700, which may be connected to one another via buses 1800.

The ultrasound imaging apparatus 1000 may be a cart type apparatus or a portable type apparatus. Examples of portable ultrasound imaging apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 1100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound imaging apparatus 1000 by wire or wirelessly, and according to embodiments, the ultrasound imaging apparatus 1000 may include a plurality of probes 20.

A transmitter 1110 supplies a driving signal to the probe 20. The transmitter 110 includes a pulse generator 1112, a transmission delaying unit 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 may include an amplifier 1122, an analog-to-digital converter (ADC) 1124, a reception delaying unit 1126, and a summing unit 1128. The amplifier 1122 amplifies echo signals in each channel, and the ADC 1124 performs analog-to-digital conversion with respect to the amplified echo signals. The reception delaying unit 1126 delays digital echo signals output by the ADC 124 by delay times necessary for determining reception directionality, and the summing unit 1128 generates ultrasound data by summing the echo signals processed by the reception delaying unit 1166. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform. The image processor 1200 may include at least one selected from the group consisting of a processor, a central processing unit (CPU), a microprocessor, and a graphic processing unit (GPU), which process at least one function. The image processor 1200 may include a plurality of modules, and each of the plurality of modules may process at least one function. The at least one processor included in the image processor 1200 may be coupled to the memory 1500 to execute instructions stored in the memory 1500. As illustrated in FIG. 1, the image processor 1200 and the controller 1700 may be embodied separately. In an exemplary embodiment, the image processor 1200 may be at least a part of the controller 1700.

A B mode processor 1212 included in a data processor 1210 extracts B mode components from ultrasound data and processes the B mode components. An image generator 1220 may generate an ultrasound image indicating signal intensities as brightness based on the extracted B mode components 1212.

Similarly, a Doppler processor 1214 included in the data processor 1210 may extract Doppler components from ultrasound data, and the image generator 1220 may generate a Doppler image indicating a movement of an object as colors or waveforms based on the extracted Doppler components.

According to an embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

A display 1400 displays the generated ultrasound image. The display 1400 may display not only an ultrasound image, but also various pieces of information processed by the ultrasound imaging apparatus 1000 on a screen image via a graphical user interface (GUI). In addition, the ultrasound imaging apparatus 1000 may include two or more displays 1400 according to embodiments.

The communication module 1300 is connected to a network 30 by wire or wirelessly to communicate with an external device or a server. The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 1300 may receive information about a diagnosis history or medical treatment schedule of a patient from a server and utilizes the received information to diagnose the patient. Furthermore, the communication module 1300 may perform data communication not only with a server or a medical apparatus in a hospital, but also with a portable terminal of a medical doctor or patient.

The communication module 1300 is connected to the network 30 by wire or wirelessly to exchange data with a server 32, a medical apparatus 34, or a portable terminal 36. The communication module 1300 may include one or more components for communication with external devices. For example, the communication module 1300 may include a local area communication module 1310, a wired communication module 1320, and a mobile communication module 1330.

The local area communication module 1310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electric signals or optical signals. Examples of wired communication techniques according to an embodiment may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound imaging apparatus 1000. For example, the memory 1500 may store medical data related to diagnosis of an object, such as ultrasound data and an ultrasound image that are input or output, and may also store algorithms or programs which are to be executed in the ultrasound imaging apparatus 1000. For example, the memory 1500 may store one or more instructions executable by at least one processor.

The memory 1500 may be any of various storage media, e.g., a flash memory, a hard disk drive, EEPROM, etc. Furthermore, the ultrasound imaging apparatus 1000 may utilize web storage or a cloud server that performs the storage function of the memory 1500 online.

The input device 1600 refers to a means via which a user inputs data for controlling the ultrasound imaging apparatus 1000. The input device 1600 may include hardware components, such as a keypad, a mouse, a touch pad, a touch screen, and a jog switch. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 1700 may control all operations of the ultrasound imaging apparatus 1000. In other words, the controller 1700 may control operations among the probe 20, the ultrasound transceiver 1100, the image processor 1200, the communication module 1300, the display 1400, the memory 1500, and the input device 1600 shown in FIG. 1. The controller 1700 may include at least one selected from the group consisting of a processor, a CPU, a microprocessor, and a GPU, which process at least one function. The controller 1700 may include a plurality of modules, and each of the plurality of modules may process at least one function. The at least one processor included in the controller 1700 may be coupled to the memory 1500 to execute instructions stored in the memory 1500. As illustrated in FIG. 1, the controller 1700 and the image processor 1200 may be embodied separately. In an exemplary embodiment, the controller 1700 may be at least a part of the image processor 1200.

All or some of the probe 20, the ultrasound transceiver 1100, the image processor 1200, the communication module 1300, the display 1400, the memory 1500, the input device 1600, and the controller 1700 may be implemented as software modules. Furthermore, at least one selected from the ultrasound transceiver 1100, the image processor 1200, and the communication module 1300 may be included in the controller 1700. However, embodiments of the present invention are not limited thereto.

Figure 2:
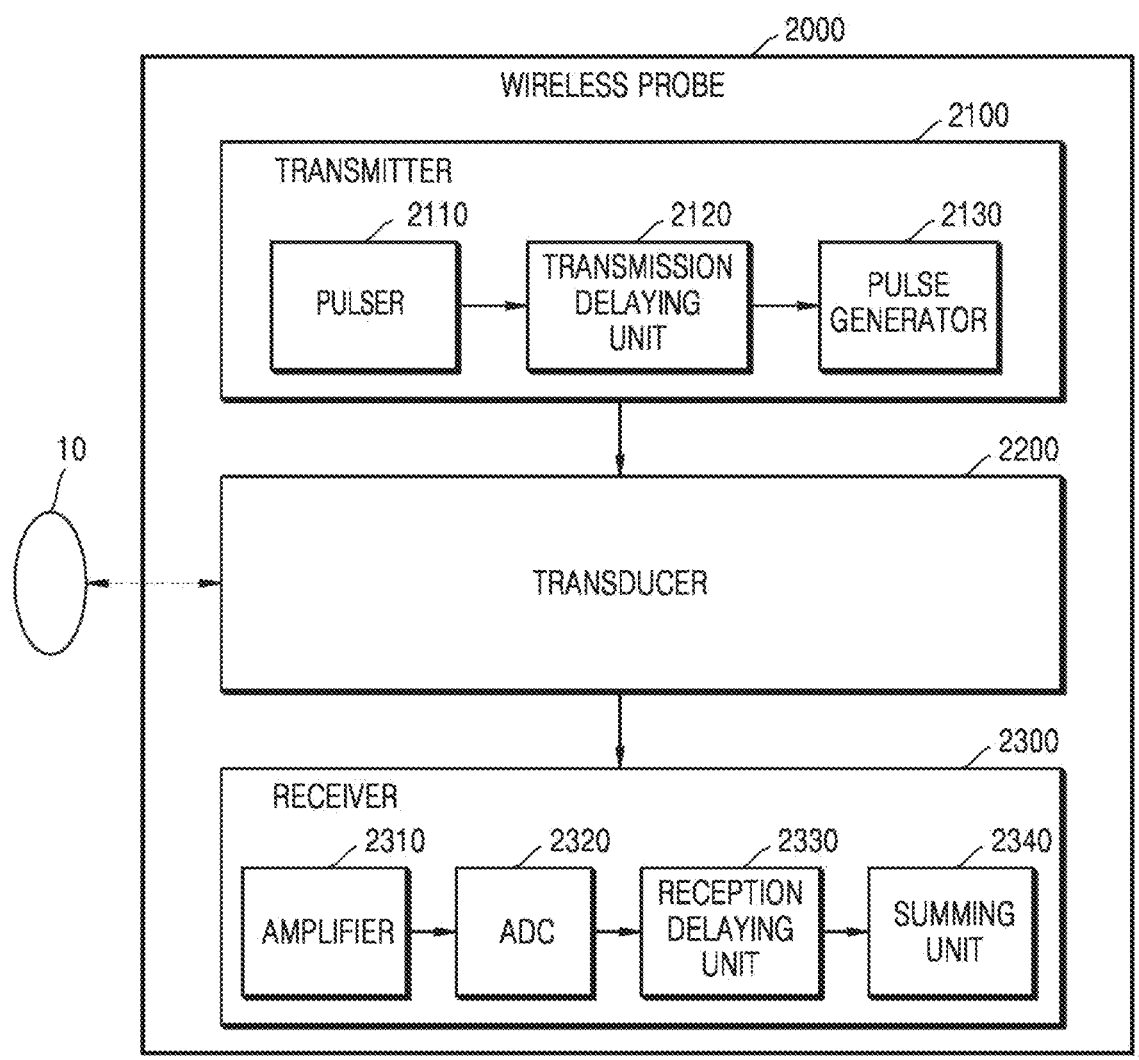
FIG. 2 is a block diagram of a configuration of a wireless probe according to an embodiment.

FIG. 2 is a block diagram of a configuration of a wireless probe 2000 according to an embodiment.

As described above with reference to FIG. 1, the wireless probe 2000 may include a plurality of transducers, and, according to embodiments, may include some or all of the components of the ultrasound transceiver 100 shown in FIG. 1.

The wireless probe 2000 according to the embodiment shown in FIG. 2 includes a transmitter 2100, a transducer 2200, and a receiver 2300. Since descriptions thereof are given above with reference to FIG. 1, detailed descriptions thereof will be omitted here. In addition, according to embodiments, the wireless probe 2000 may selectively include a reception delaying unit 2330 and a summing unit 2340.

The wireless probe 2000 may transmit ultrasound signals to the object 10, receive echo signals from the object 10, generate ultrasound data, and wirelessly transmit the ultrasound data to the ultrasound imaging apparatus 1000 shown in FIG. 1.

Figure 3:
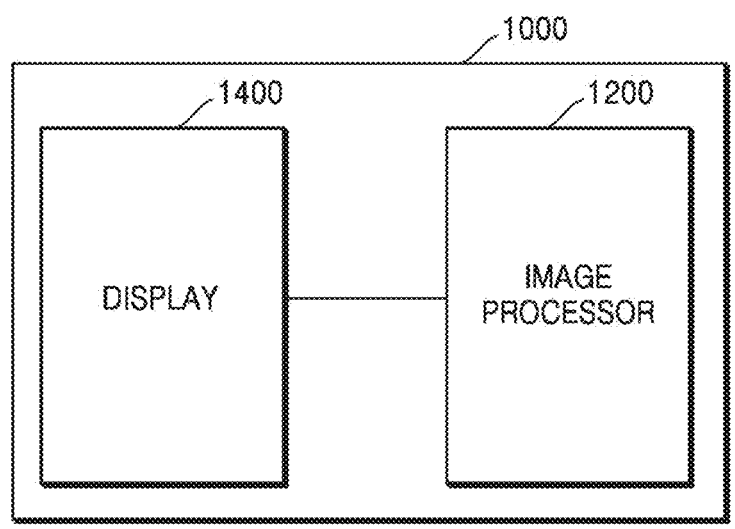
FIG. 3 is a block diagram of an ultrasound imaging apparatus according to an embodiment.

FIG. 3 is a block diagram of a configuration of an ultrasound imaging apparatus 1000 according to an embodiment.

Referring to FIG. 3, the ultrasound imaging apparatus 1000 may include an image processor 1200 and a display 1400. However, all of the components shown in FIG. 3 are not essential components. The ultrasound imaging apparatus 1000 may include more or fewer components than those shown in FIG. 3.

The image processor 1200 may process ultrasound image data according to an image display mode. The image processor 1200 may acquire brightness (B) mode data by performing processing such as amplification, logarithmic compression, and envelope detection on echo signals reflected from an object or obtain contrast enhanced mode data by intravenously injecting ultrasound contrast medium containing microbubbles into the object.

The image processor 1200 may use strong nonlinear effects of an ultrasound contrast medium in a contrast enhanced ultrasound (CEUS) mode. Due to the nonlinear effects of ultrasound contrast medium, waves reflected from microbubbles are greatly distorted compared to incident waves, which causes generation of harmonic components. Based on the above characteristics, the image processor 1200 may use a contrast harmonic imaging technique to suppress fundamental waves by imaging a harmonic wave having a frequency twice the frequency of fundamental waves while the ultrasound contrast medium is further enhanced. By using the contrast harmonic imaging technique, it is possible to obtain an image in which waves reflected from a contrast medium are enhanced since waves reflected from microbubbles contain more second harmonic wave components than waves reflected from a biological tissue.

The image processor 1200 may generate a first image showing tissue of the object based on echo signals reflected from the object. In an exemplary embodiment, the first image may be a B mode ultrasound image.

The image processor 1200 may generate, based on echo signals reflected by the object, a second image showing contrast medium injected into the object. In an exemplary embodiment, the second image may be a contrast enhanced ultrasound image. The second image may be generated based on echo signals reflected from the contrast medium injected into the object.

During generation of the second image, a signal reflected due to a movement of the tissue of the object may interfere with a signal reflected by the ultrasound contrast medium, which may degrade the contrast of blood vessels in the second image. To mitigate this effect of the signal reflected due to the movement of the tissue of the object, an intensity of the signal may be supressed during signal processing. However, according to this method, the intensity of the signal may be suppressed insufficiently.

To solve these problems, the image processor 1200 may generate a third image by removing at least a portion of a tissue from the second image based on the first image. Like the second image, the third image may be a contrast-enhanced ultrasound image. A method of removing at least a portion of a tissue from the second image based on the first image will be described in more detail below with reference to FIGS. 4A and 4B.

The third image from which at least a portion of the tissue is removed may exhibit improved contrast of blood vessels in comparison to the second image.

The display 1400 may display 2D and/or 3D ultrasound images. Furthermore, the display 1400 may display the first image together with the second or third image. For example, the display 1400 may display a B mode ultrasound image together with a contrast-enhanced ultrasound image or an improved contrast-enhanced ultrasound image.

Figure 4A:
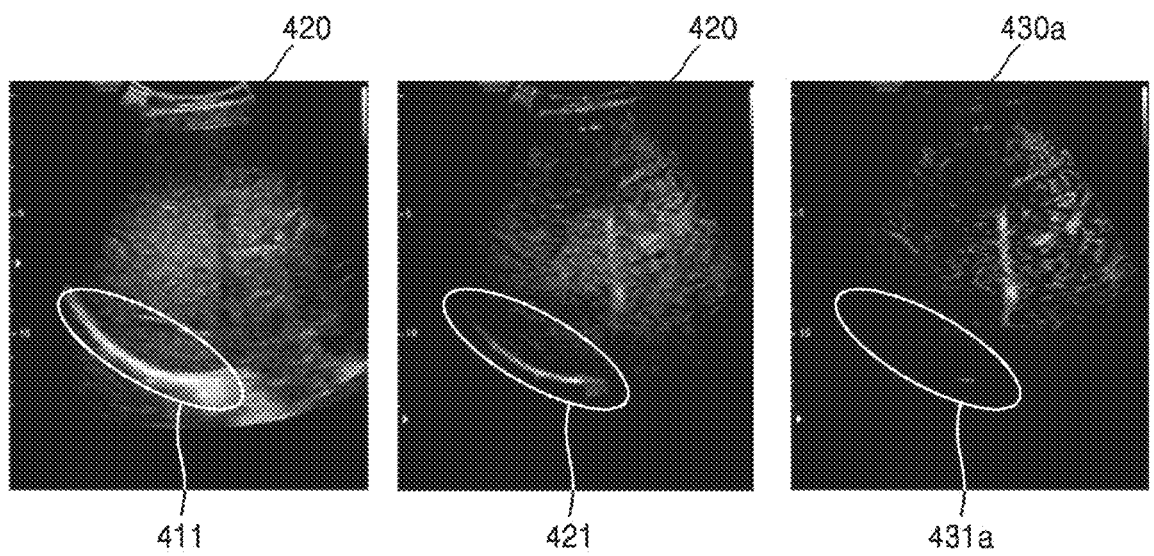
FIG. 4A is an exemplary diagram of first through third images according to an embodiment.

FIG. 4A is an exemplary diagram of first through third images 410, 420, and 430*a* according to an embodiment.

Referring to FIG. 4A, the first and second images 410 and 420 may respectively show tissues 411 and 421. In the first and second images 410 and 420, the tissues 411 and 412 may appear brighter than other regions. The first and second images 410 and 420 may be a B mode ultrasound image and a contrast-enhanced ultrasound image, respectively.

The image processor 1200 may generate the third image 430*a* by removing at least a portion of a tissue from the second image 420 based on the first image 410. Similar to the second image 420, the third image 430*a* may be a contrast-enhanced ultrasound image.

According to an embodiment, the image processor 1200 may generate the third image 430*a* by removing from the second image 420 a portion of a tissue which the first and second images 410 and 420 have in common. For example, as shown in FIG. 4A, the image processor 1200 may generate the third image 430*a* by removing tissue 421 from the second image 420.

As shown in FIG. 4A, a portion 431*a* in the generated third image 430*a* corresponding to the tissue 421 in the second image 420 may be significantly suppressed.

According to an embodiment, to remove a portion which the first and second images 410 and 420 have in common from the second image 420, the image processor 1200 may perform image subtraction by subtracting the first image 410 from the second image 420. The third image 430*a* may be generated as a result of performing the image subtraction. The generated third image 430*a* may be less affected by the tissue 411 in the first image 410 than the second image 420. Since a portion which the first and second images 410 and 420 have in common is removed and is not shown in the third image 430*a*, the third image 430*a* may exhibit improved contrast of blood vessels in comparison to the second image 420.

According to an embodiment, a portion shown in the second image 420 but not in the first image 410 may be emphasized in the third image 430*a*. For example, blood vessels depicted by a contrast medium may be emphasized in the third image 430*a*.

FIG. 4B is an exemplary diagram of third and fourth images 430*a* and 430*b* according to an embodiment.

Referring to FIGS. 4A and 4B, the image processor 1200 may generate the fourth image 430*b* by removing at least a portion of a tissue from the second image 420 based on the first image 410. Portions removed from the second image 420 in order to generate the third and fourth images 430*a* and 430*b* may have different sizes. For example, as shown in 431*a* and 431*b* of FIG. 4B, a portion removed in order to generate the fourth image 430*b* may be larger than a portion removed in order to generate the third image 430*a*. Like the second image 420, the third and fourth images 430*a* and 430*b* may both be contrast-enhanced ultrasound images.

FIG. 5 is an exemplary diagram of a user interface (UI) for displaying a plurality of contrast-enhanced ultrasound images, according to an embodiment As shown in FIG. 5, the display 1400 may alternately display a plurality of contrast-enhanced ultrasound images 530 based on a user input. In this case, sizes of the portions removed based on a B mode ultrasound image 510 may vary across the plurality of contrast-enhanced ultrasound images 530. For example, the plurality of contrast-enhanced ultrasound images 530 may be displayed alternately on the display 1400 in an order from a contrast-enhanced ultrasound image 530*a* from which a portion overlapping with the B mode ultrasound image 510 is not removed, to a contrast-enhanced ultrasound image 530*d* from which a portion overlapping with the B mode ultrasound image 510 is removed, the portion being larger than other portions of contrast-enhanced ultrasound images 530*a*, 530*b*, and 530*c*. In this case, a lowest weight may be assigned to the contrast-enhanced ultrasound image 530*a*, and a highest weight may be assigned to the contrast-enhanced ultrasound image 530*d*.

In this case, the user input may be received by the ultrasound imaging apparatus 100 via the input device 1600. For example, if a user input for increasing "FlowMAX index" is received by the ultrasound imaging apparatus 1000 via the input device 1600, the display 1400 may display a contrast-enhanced ultrasound image with the portion overlapping with the B mode ultrasound image 510 removed to a greater extent. If a user input for decreasing "FlowMax Index" is received by the ultrasound imaging apparatus 1000, the display 1400 may display a contrast-enhanced ultrasound image with the portion overlapping with the B mode ultrasound image 510 removed to a lesser extent or to no extent.

Although FIG. 5 shows that the input device 1600 is a touch screen, the input device 1600 may be implemented as a jog switch.

Figure 6:
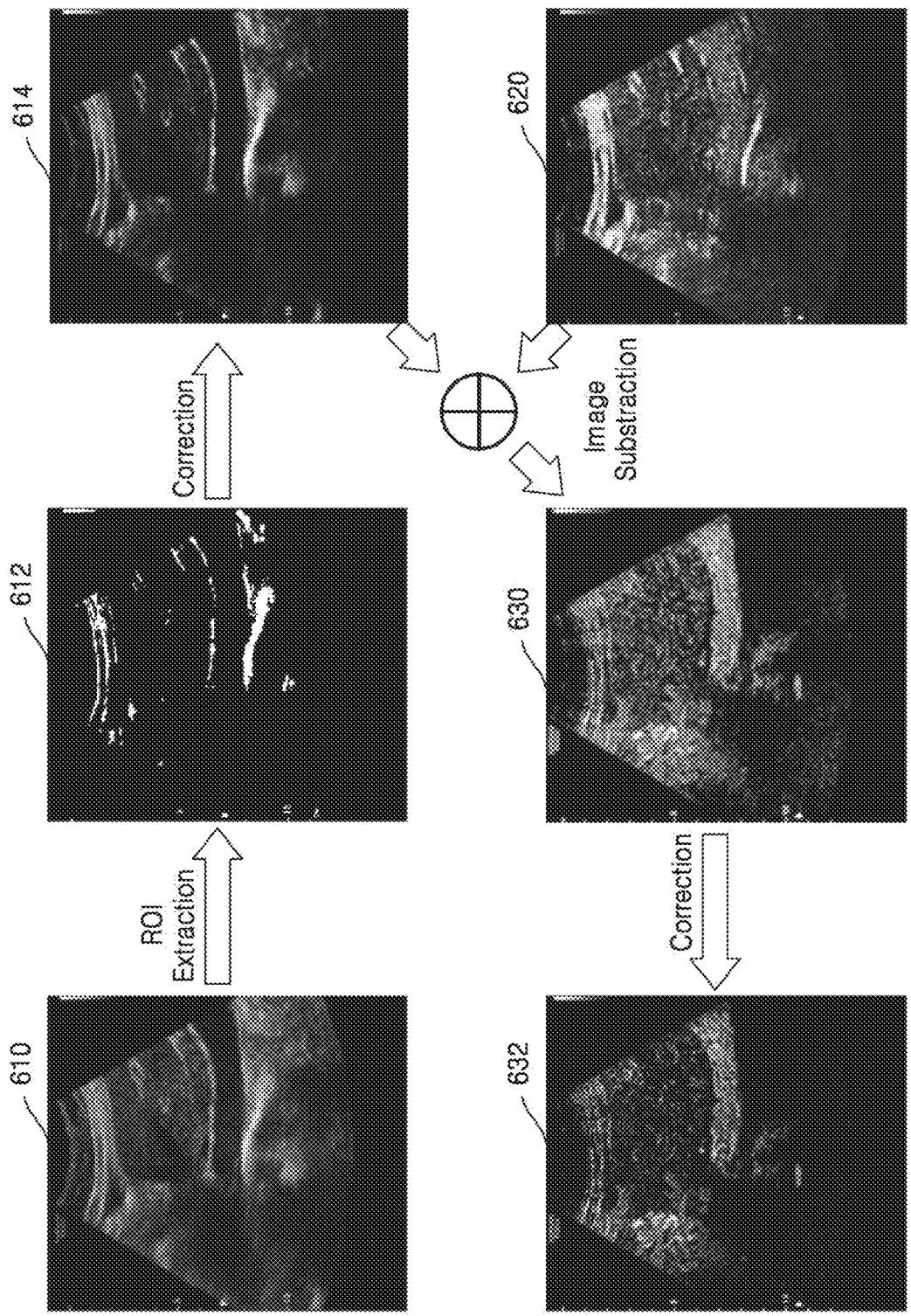
FIG. 6 is a diagram for explaining a method of generating a third image according to an embodiment.

FIG. 6 is a diagram for explaining a method of generating a third image according to an embodiment.

Referring to FIG. 6, the image processor 1200 may extract a region of interest (ROI) from a first image 610. The ROI may be extracted based on a predetermined criterion. For example, a region having a brightness that is greater than or equal to a predetermined threshold value in the first image 610 may be extracted as the ROI.

A white mask 612 may be detected by extracting regions having a brightness that is greater than or equal to the predetermined threshold value from the first image 610.

According to an embodiment, at least one of the first and second images 610 and 620 may be corrected so that regions corresponding to the white mask 612 in the first and second images 610 and 620 have the same average brightness. For example, the first image 610 may be normalized so that regions corresponding to the white mask 612 in the normalized first image 614 and the second image 620 have the same average brightness. Since at least one of the first and second images 610 and 620 is normalized so that regions corresponding to the white mask 612 in the first and second images 610 and 620 have an equal average brightness, image subtraction may be performed by subtracting the normalized first image 614 from the second image 620. After preforming the image subtraction, a third image 630 may be generated by removing the region corresponding to the white mask 612 in the second image 620.

According to an embodiment, by removing the region corresponding to the white mask 612 in the second image 620, tissues other than blood vessels may be removed from the second image 620. Thus, the third image 630 may exhibit improved contrast of blood vessels compared to other contrast-enhanced ultrasound images as well as the second image 620.

In an embodiment, a decrease in an intensity of a B mode signal due to injection of a contrast medium may offset saturation of a contrast-enhanced signal by adjusting image parameters of the third image 630. For example, a brightness of the third image 630 may be adjusted. In this case, the brightness of the third image 630 may be adjusted based on a threshold value, a minimum value, a maximum value, etc.

For example, the third image 630 may be corrected so that a brightness of the third image 630 is approximately equal to that of the second image 620. As shown in FIG. 6, since a brightness of a corrected third image 632 approximates that of the second image, the corrected third image 632 may appear darker than the third image 630.

By adjusting the brightness of the third image 630, speckles in the third image 630 and flickering caused by regions removed from the second image 620 may be eliminated. For example, if the plurality of contrast-enhanced ultrasound images 530 displayed as shown in FIG. 5 have different brightnesses, speckles may occur and flickering may be caused by a change of removed regions. According to an embodiment, by adjusting brightness of the plurality of contrast-enhanced ultrasound images 530, speckles and flickering may be suppressed in the plurality of contrast-enhanced ultrasound images 530.

Figure 7:
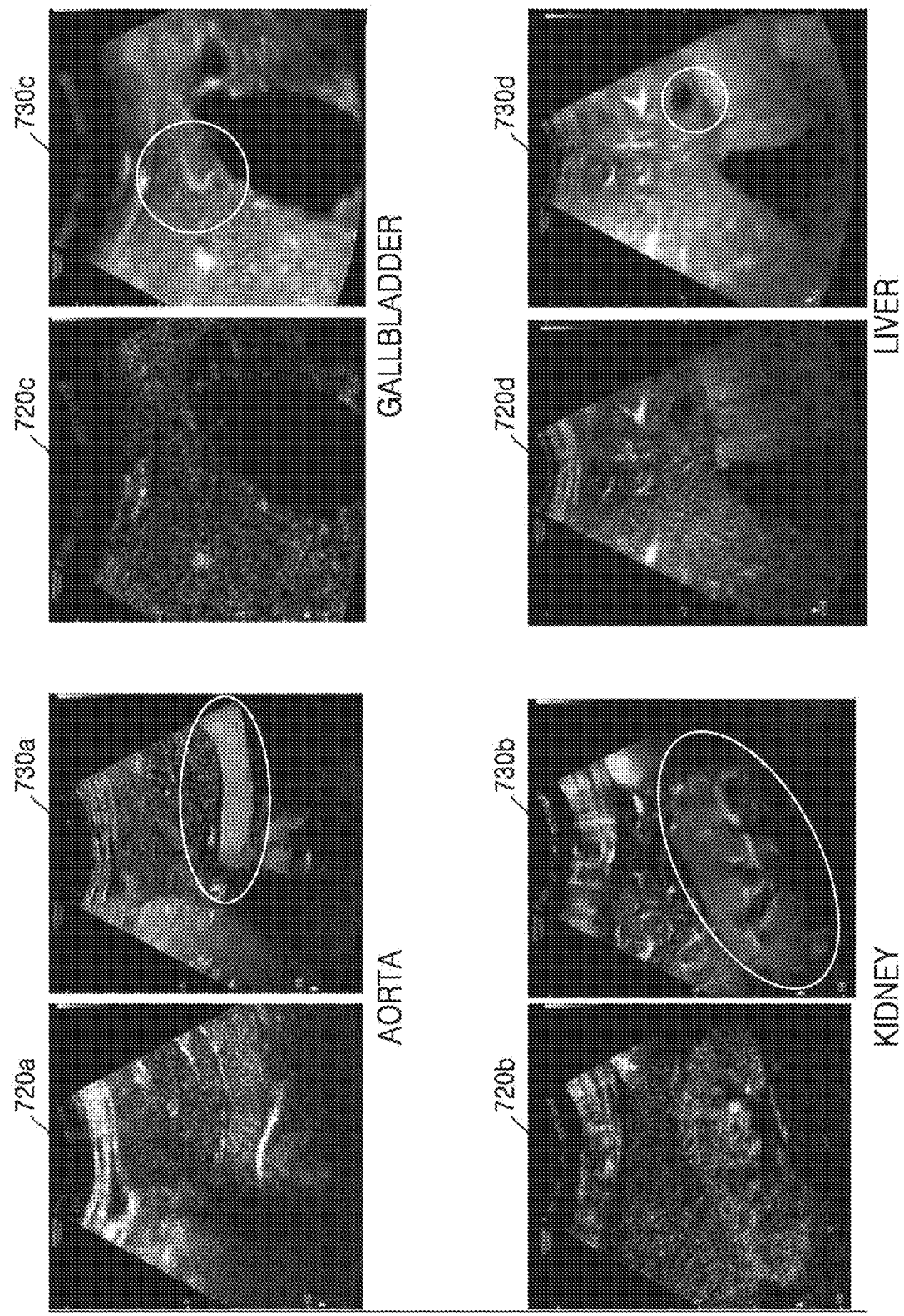
FIG. 7 illustrates second and third images of different body parts according to an embodiment.

FIG. 7 illustrates second and third images of different body parts according to an embodiment.

Referring to FIG. 7, according to an embodiment, second and third images 720a and 730a showing an aorta, second and third images 720b and 730b showing a kidney 720b and 730b, second and third images 720c and 730c showing a gallbladder, and second and third images 720d and 730d showing a liver may be generated.

The third image 730a of the aorta shows improved distinguishability between blood vessels and tissue compared to the second image 720a. In detail, by darkening tissue that appears bright in the second image 720a in the third image 730a, distinguishability between blood vessels and tissue is improved in the third image 730a. Furthermore, as shown in a white-rimmed oval shape within the third image 730a, the aorta that is difficult to distinguish in the second image 720a is clearly depicted in the third image 730a.

The third image 730b of the kidney shows improved distinguishability between blood vessels and tissue compared to the second image 720b. In detail, as shown in a white-rimmed oval shape within the third image 730b, the shape of the kidney is clearly defined so that the kidney is easily distinguishable from other body parts. Furthermore, blood vessels in the kidney are more clearly depicted in the third image 730b than in the second image 720b.

The third image 730c of the gallbladder shows improved distinguishability between blood vessels and tissue compared to the second image 720c. In detail, as shown in a white-rimmed oval shape within the third image 730c, polyps may appear in the third image 730c and a boundary of the gallbladder in the third image 730c is more clearly defined than in the second image 720c.

The third image 730d of the liver shows improved distinguishability between blood vessels and tissue compared to the second image 720d. In detail, as shown in a white-rimmed oval shape within the third image 730d, polyps may appear, and a boundary of metastatic cancer is more clearly defined than in the second image 720d.

Figure 8:
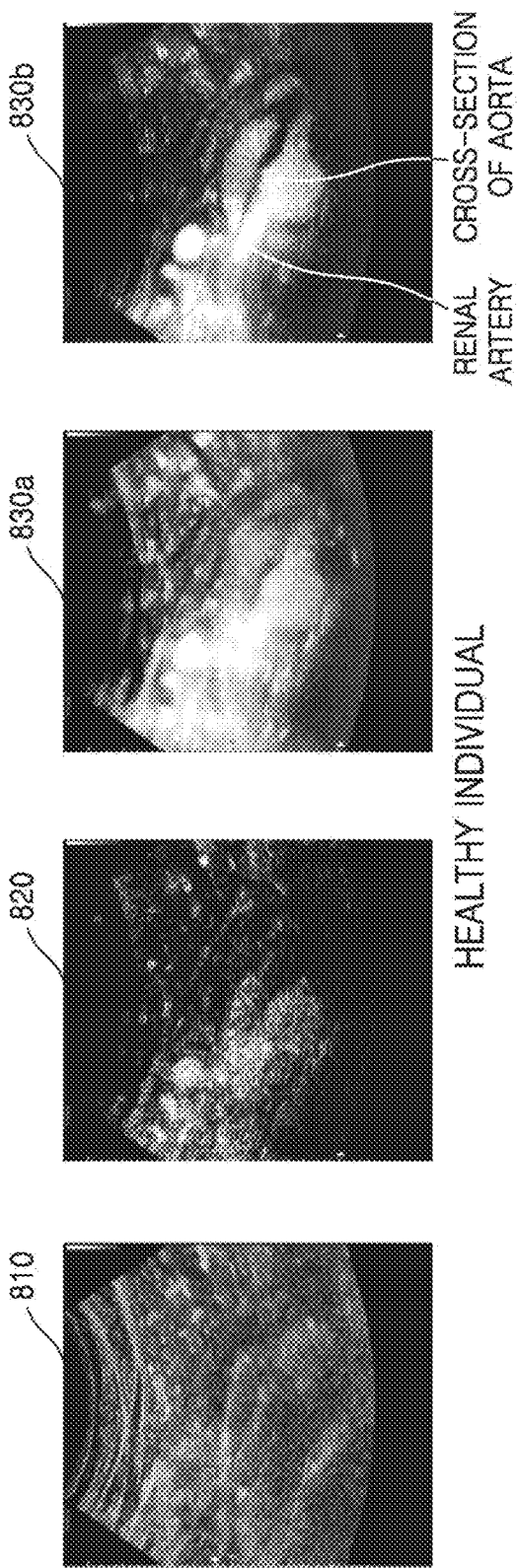
FIG. 8 illustrates first through fourth images obtained in the case of a healthy individual, according to an embodiment.
Figure 9:
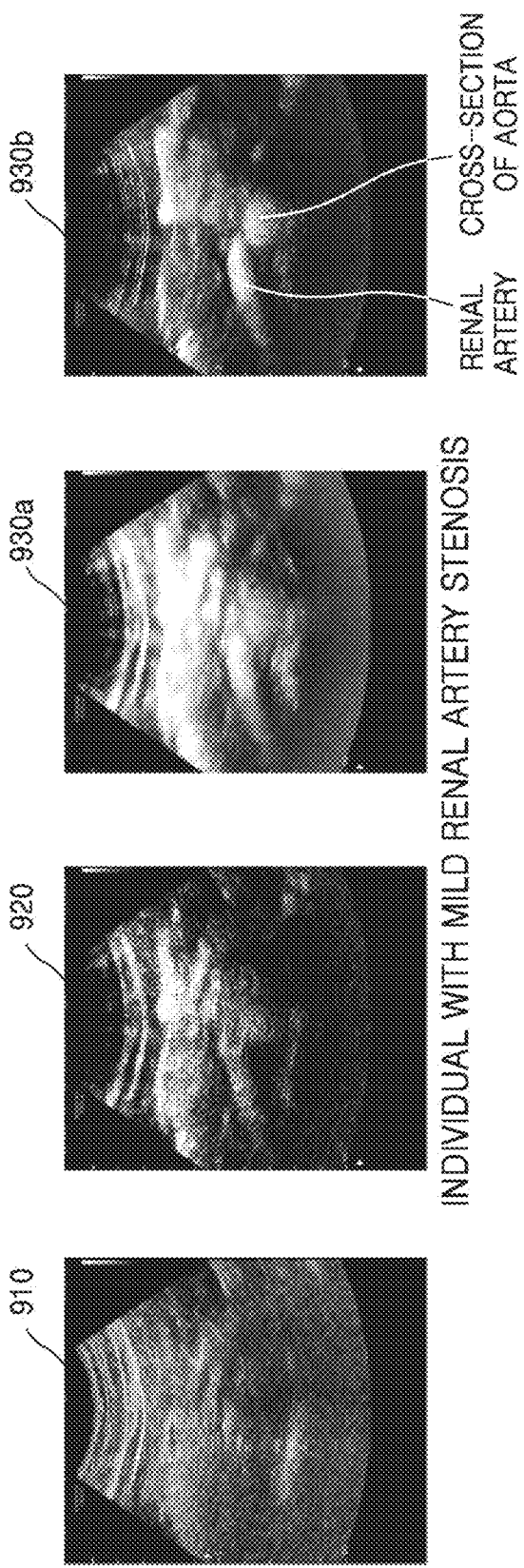
FIG. 9 illustrates first through fourth images obtained in the case of an individual with mild renal artery stenosis, according to an embodiment.

FIG. 8 illustrates first through fourth images obtained in the case of a healthy individual, according to an embodiment, and FIG. 9 illustrate first through fourth images obtained in the case of an individual with mild renal artery stenosis, according to an embodiment.

As shown in FIGS. 8 and 9, first images 810 and 910, second images 820 and 920, third images 830a and 930a, and fourth images 830b and 930b may be generated by an ultrasound imaging apparatus according to an embodiment. Renal arteries and cross-sections of aorta are more clearly depicted in the fourth images 830b and 930b with improved contrast of blood vessels than in the other contrast-enhanced ultrasound images 820, 920, 830a, and 930a.

Figure 10:
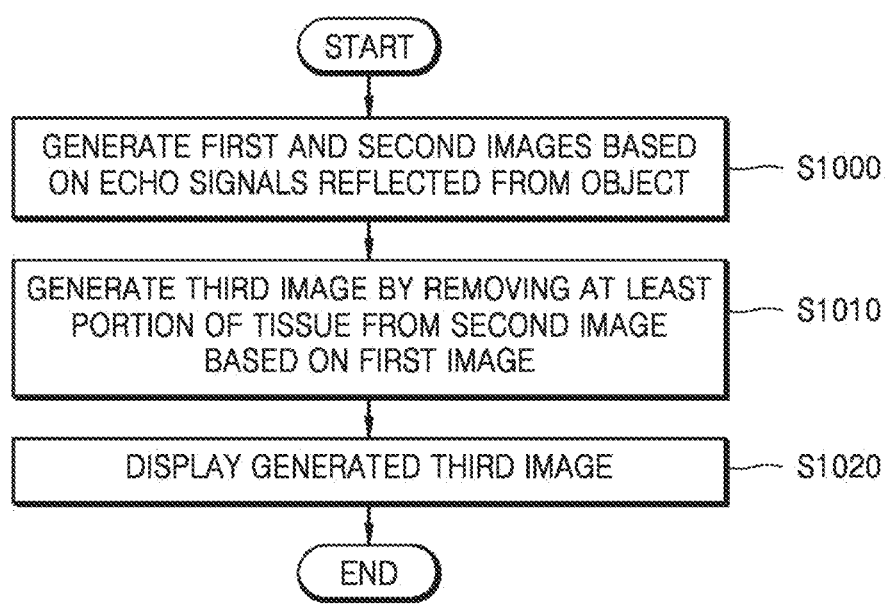
FIG. 10 is a flowchart of a method of generating a third image according to an embodiment.

FIG. 10 is a flowchart of a method of generating a third image according to an embodiment.

An image processor of an ultrasound imaging apparatus generates first and second images based on echo signals reflected from an object (S1000).

The first image mainly shows tissue of the object, and the second image mainly shows a contrast medium injected into the object. In this case, the first and second images may be a B mode ultrasound image and a contrast-enhanced ultrasound image, respectively.

The image processor generates a third image by removing at least a portion of a tissue from the second image based on the first image (S1010).

According to an embodiment, the image processor may generate the third image by removing a portion which the first and second images have in common from the second image.

According to an embodiment, in order to remove the portion which the first and second images have in common from the second image, the image processor may perform image subtraction by subtracting the first image from the second image.

According to an embodiment, a portion shown in the second image but not in the first image may be emphasized in the third image. For example, blood vessels depicted by a contrast medium may be emphasized in the third image.

According to an embodiment, the image processor may extract an ROI from the first image. The ROI may be extracted based on a predetermined criterion. For example, a region having a brightness that is greater than or equal to a predetermined threshold value in the first image may be extracted as the ROI.

A white mask may be detected by extracting regions having a brightness that is greater than or equal to a predetermined threshold value from the first image.

According to an embodiment, the image processor may correct at least one of the first and second images so that regions corresponding to the white mask in the first and second images have the same average brightness.

In an embodiment, a decrease in intensity of a B mode signal due to injection of a contrast medium may offset saturation of a contrast-enhanced signal by adjusting image parameters of the third image. For example, a brightness of the third image may be adjusted based on a threshold value, a minimum value, a maximum value, etc.

A display of the ultrasound imaging apparatus displays the third image generated in operation S1010 (S1020).

The third image may be displayed parallel to the first image. Furthermore, as described above with reference to FIG. 5, the third image as a contrast-enhanced ultrasound image may be displayed alternately with other contrast-enhanced ultrasound images.

Embodiments may be implemented through non-transitory computer-readable recording media having recorded thereon computer-executable instructions such as program modules that are executed by a computer. The non-transitory computer-readable recording media may be any available media that can be accessed by a computer and include both volatile and nonvolatile media and both detachable and non-detachable media. Furthermore, the non-transitory computer-readable recording media may include computer storage media and communication media. The computer storage media include both volatile and nonvolatile and both detachable and non-detachable media implemented by any method or technique for storing information such as computer-readable instructions, data structures, program modules, or other data. The communication media typically embody computer-readable instructions, data structures, program modules, other data of a modulated data signal, or other transmission mechanism, and may include any information transmission media While one or more embodiments have been described with reference to the figures, it will be understood by those of ordinary skill in the art that various changes in form and details may be made therein without departing from the spirit and scope of the inventive concept as defined by the following claims.

What is claimed is:

1. An ultrasound imaging apparatus comprising:
a memory configured to store instructions; and
at least one processor configured to execute the stored instructions to:
generate, based on echo signals reflected from an object, a first image of a first imaging characteristic for showing a tissue of the object;
generate, based on fundamental or harmonic components of signals reflected from the object, a series of second images of a second imaging characteristic, which is different from the first imaging characteristic, for showing a contrast medium injected into the object along a period of time;
generate a series of sets of third images corresponding to the series of second images along the period of time by removing, by performing image subtraction of subtracting the first image of the first imaging characteristic from each of the second images of the second imaging characteristic, the tissue from each of the second images of the second imaging characteristic, wherein a sequential order among a set of third images corresponding to a second image corresponds to an extent of removal of the tissue from the second image; and
in response to receiving a user input for increasing or decreasing the extent of removal of the tissue from the second image, display, respectively, the set of third images according to the sequential order, wherein the extent of removal of the tissue varies among the set of third images.

2. The ultrasound imaging apparatus of claim 1, wherein the tissue to be removed has a brightness greater than or equal to a threshold value in the first image.

3. The ultrasound imaging apparatus of claim 1, wherein the first image and the second image have the tissue to be removed in common.

4. The ultrasound imaging apparatus of claim 3, wherein the processor is further configured to execute the stored instructions to correct at least one of the first image and the second image so that the tissue to be removed has the same brightness in the first image and the second image.

5. The ultrasound imaging apparatus of claim 4, the tissue is removed from the second image based on adjusting a weight for the tissue in the first image and the second image.

6. The ultrasound imaging apparatus of claim 5, wherein the processor is further configured to execute the stored instructions to correct the set of third images so that brightnesses of the set of third images are approximately equal to a brightness of the second image.

7. The ultrasound imaging apparatus of claim 1, wherein a portion shown in the second image but not shown in the first image is more emphasized in the set of third images as the extent of removal of the issue increases.

8. The ultrasound imaging apparatus of claim 1, wherein the processor is further configured to execute the stored instructions to correct the set of third images to equalize image parameters of the set of third images.

9. The ultrasound imaging apparatus of claim 1, wherein the first imaging characteristic is a brightness (B) mode ultrasound imaging characteristic, and the second imaging characteristic is a contrast enhanced ultrasound (CEUS) mode imaging characteristic.

10. A method comprising:
generating, based on echo signals reflected from an object, a first image of a first imaging characteristic for showing a tissue of the object;
generating, based on fundamental or harmonic components of signals reflected from the object, a series of second images of a second imaging characteristic, winch is different from the first imaging characteristic, for showing a contrast medium injected into the object along a period of time;
generating a series of sets of third images corresponding to the series of second images along the period or time by removing, by performing image subtraction of subtracting the first image of the first imaging characteristic from each of the second images of the second imaging characteristic, the tissue from each of the second images of the second imaging characteristic, wherein a sequential order among a set of third images corresponding to a second image corresponds to an extent or removal of the tissue from the second image; and
in response to receiving a user input for increasing or decreasing the extent of removal of the tissue from the second image, displaying, respectively, the set of third images according to the sequential order, wherein the extent of removal of the tissue varies among the set of third images.

11. The method of claim 10, wherein the tissue to be removed has a brightness greater than or equal to a threshold value in the first image.

12. The method of claim 10, wherein the first image and the second image have the tissue to be removed in common.

13. The method of claim 12, further comprising correcting at least one of the first image and the second image so that the tissue to be removed has same brightness in the first image and the second image.

14. The method of claim 13, wherein the tissue is removed from the second image based on adjusting a weight for the tissue in the first image and the second image.

15. The method of claim 14, further comprising correcting the set of third images so that brightnesses of the set of third images are approximately equal to a brightness of the second image.

16. The method of claim 10, wherein a portion shown in the second image but not shown in the first image is more emphasized in the set of third images as the extent of removal of the tissue increases.

17. The method of claim 1, further comprising correcting the set of third images to equalize image parameters of the set of third images.

18. A computer-readable recording medium having recorded thereon a program for executing the method of claim 10 on a computer.

19. The method of claim 10, wherein the first imaging characteristic is a brightness (B) mode ultrasound imaging characteristic, and the second imaging characteristic is a contrast enhanced ultrasound (CEUS) mode imaging characteristic.

* * * * *